United States Patent [19]

Whitehead

[11] Patent Number: 4,578,263
[45] Date of Patent: Mar. 25, 1986

[54] PHARMACEUTICAL PELLET

[75] Inventor: Derek J. Whitehead, Poynton, England

[73] Assignee: Castex Products Limited, Macclesfield, England

[21] Appl. No.: 661,417

[22] Filed: Oct. 16, 1984

[30] Foreign Application Priority Data

Oct. 28, 1983 [GB] United Kingdom ............... 8328916

[51] Int. Cl.$^4$ ........................... A61J 3/00; A61K 9/22
[52] U.S. Cl. ......................................... 424/15; 119/1;
119/51 R; 604/890; 604/892; 424/14; 424/16;
424/19; 424/21; 424/22
[58] Field of Search ............... 119/1, 51 R; D28/2;
604/890, 892; 424/14, 16, 19, 21, 22, 15

[56] References Cited

U.S. PATENT DOCUMENTS

| D. 14,842 | 3/1884 | Griscom | D28/2 |
| 3,056,724 | 10/1962 | Marston | 604/892 |
| 3,567,818 | 3/1971 | Hemingway et al. | 424/14 |
| 3,594,469 | 7/1971 | Whitehead et al. | 424/14 |
| 3,964,438 | 6/1976 | Rodemeyer | 119/1 |
| 4,308,250 | 12/1981 | Griffin et al. | 424/16 |
| 4,381,780 | 5/1983 | Holloway | 604/892 |

FOREIGN PATENT DOCUMENTS

| 942667 | 2/1974 | Canada | 604/892 |
| WO82/094 | 1/1982 | PCT Int'l Appl. | |
| 2020181 | 11/1979 | United Kingdom. | |
| 1603970 | 12/1981 | United Kingdom. | |
| 2115073 | 9/1983 | United Kingdom. | |

Primary Examiner—Ronald W. Griffin
Attorney, Agent, or Firm—Donald Brown; Robert T. Gammons

[57] ABSTRACT

A pellet for administration into and reside in the rumeno-reticular sac of a ruminant and to release successive doses of an active agent, such as an anthelmentic, comprises an assembly (10) of discs (12) each having a peripheral skirt (14) on one side and an inwardly-spaced skirt (16) on the other so that such discs can interfit by said skirts (14, 16) and define therebetween cavities (18) each containing a respective active agent dose (24). A weighting slug (20) is provided at one end of the assembly (10) which is enclosed except at one end by a surrounding plastics sheath (26) so that rumen juices may attack and erode the successive discs (12) to release the successive doses (24). The discs (12) are of a magnesium-based alloy and the slug (20) is of a Zinc-based alloy.

14 Claims, 4 Drawing Figures

PHARMACEUTICAL PELLET

This invention concerns a pharmaceutical pellet of the kind (hereinafter termed 'of the kind referred to') intended to be administered to a ruminant to reside in its rumeno-reticular sac and release predetermined quantities of one or more biologically-active substances over an extended period of time.

One known form of pellet of the kind referred to containing an active substance in the form of an anthelmintic material comprises a casing in the form of a metal tube having, as end caps, porous membranes through which the anthelmintic is discharged over an extended period of time. Disadvantages of such a pellet include its bulk, the fact that the casing may be retained within the rumen after the active substance has been fully dissipated and, most importantly, that the continuous discharge of the active substance at a low rate over an extended period tends to engender immunity in the parasites against which it is intended to be effective.

An object of the present invention is to provide an improved pharmaceutical pellet of the kind referred to in which these disadvantages are obviated or minimised.

With this object in view, the present invention provides a pharmaceutical pellet of the kind referred to comprising an assembly consisting of a plurality of plates, of a magnesium alloy, axially spaced to define cavities therebetween, a biologically-active substance in each said cavity, and a retaining water-impermeable sleeve or sheath protecting the assembly from attack by rumen juices except at one axial end or both axial ends thereof.

Preferably a weighting slug is incorporated at one axial end to ensure that the pellet will remain in the rumenoreticular sac until all of the active substance has been consumed. This weighting slug is preferably enclosed by the sleeve.

The invention will be described further, by way of example, with reference to the accompanying drawing, in which.

Figure 1:
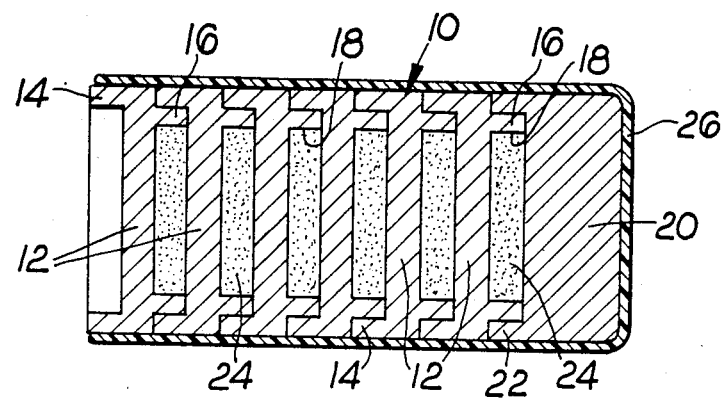
FIG. 1 is a sectional elevation illustrating a first embodiment of the pellet of the invention, the section being taken longitudinally of the pellet.

Referring firstly to FIG. 1, a first embodiment of the pharmaceutical pellet conforming to the present invention comprises an assembly, indicated generally by the reference numeral 10, consisting of a plurality of circular plates or discs 12, of a magnesium alloy (whose composition will be discussed in greater detail hereinafter) each formed with a first axially-extending circular peripheral skirt (or flange) 14 on one of its faces and a second axially-extending circular skirt 16 on the other of its faces, the second skirt 16 being inwardly spaced from the periphery of the plate 12. As can be seen the assembly 10 comprises a plurality of the plates 12 interengaged with one another by each skirt 16 engaging into the skirt or flange 14 of the next adjacent plate 12, each skirt 16 defining a respective cavity 18 between its plate 12 and the next adjacent plate 12. Preferably the skirts 14 and 16 interengage with a tight interference fit to give mechanical strength to the assembly 10.

A relatively dense or heavy weighting slug 10 completes the assembly 10, being in the form of an end cap having a flange 22 which fits onto the exposed endmost skirt 16. This slug 20 forms a closure of the cavity 18 defined by the skirt 16 of the corresponding endmost plate 12.

Each of the cavities 18 contains a dose or filling 24 of a biologically-active substance, such as an anthelmintic material which may be in tablet, powdered, paste or other practical form.

A sheath 26 of water-impermeable plastics or similar material covers the entire outer surface of the assembly 10 save for the end thereof remote from the slug 20, which end is exposed.

In use the pellet is introduced into the rumenoreticular sac of an animal to be treated by use of an oesophageal balling gun. Whilst the pellet remains in the sac, the rumen juices dissolve the successive plates 12, in turn from the end remote from the slug 20, over a period of time, typically several weeks or even months, thus to release the successive doses 24 of the biologically-active material at timed intervals. The time taken for each plate 12 to dissolve is determined by its thickness and composition. After the last plate 12 has been dissolved, the rumen juices will eventually dissolve the slug 20, and the residual sheath 26 then becomes free to be discharged by excretion or vomiting.

Typically, for cattle, each pellet might have an overall length of 55 mm, a diameter of 28 mm and deliver seven 700 mgm doses 24 over a period of six months, although the embodiment shown in FIG. 1 is, of course, adapted only to deliver six doses and fewer than six plates 12 or more than seven such plates 12 may be embodied in different embodiments as may be desired.

The sheath 26 may be formed by dipping the assembled discs 12 (with their doses 24) and the slug 20 into a suitable resin coating. As an alternative, it may be formed by shrinking a sleeve of thermo plastics material, such as polyvinyl-chloride, thereon, or by assembling the components successively into a preformed sleeve.

Figure 2:
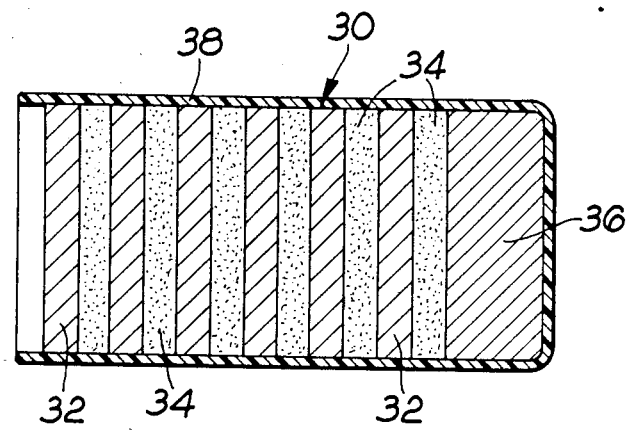
FIG. 2 is a view comparable with FIG. 1, but illustrating a second embodiment of the pellet of the invention.

Referring now to FIG. 2, the pellet here shown is generally similar to that above described. However, in this example, assembly 30 comprises plates 32 in the form of discs which do not have outwardly projecting skirts and are spaced apart by doses 34 of biologically-active material in the form of compressed tablets, one such tablet 34 being provided between one endmost plate 32 and an adjacent weighting slug in the form of a plain end plug 36. The assembly 30 is enclosed by a sheath or sleeve 38 similar to that of the embodiment of FIG. 1 as above described.

Figure 3:
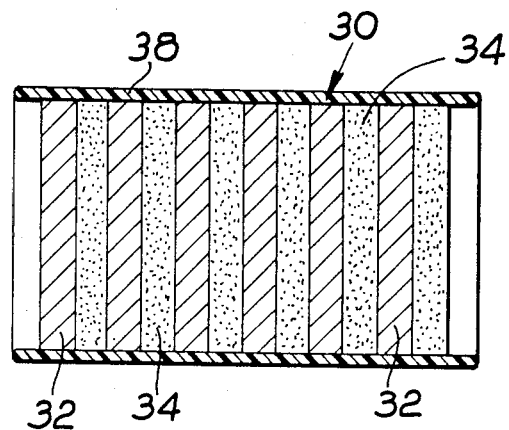
FIG. 3 is a view comparable with FIGS. 1 and 2, but showing a third embodiment.

FIG. 3 of the drawings illustrates a third embodiment of the pellet of the invention. This pellet is very similar to that of FIG. 2 and accordingly similar reference numerals have been allocated to those parts which are similar to those already described. It differs from that of FIG. 2, however, in that it does not incorporate a weighting slug and in that it has both axial ends exposed so that the doses 34 and plates 32 are dissolved from both ends of the pellet. These two features, namely the omission of the weighting slug and the exposure of the two ends of the pellet can, of course, be applied either singly or in combination to the embodiments of FIGS. 1 and 2.

Figure 4:
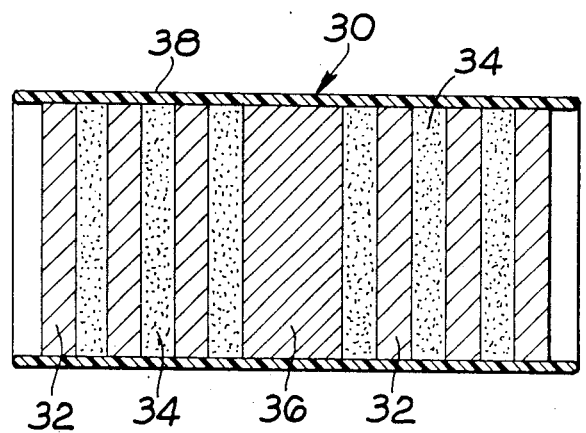
FIG. 4 is a similar view showing yet a further embodiment.

The embodiment of FIG. 4 is similar to that of FIG. 3, and again similar reference numerals have been allocated to similar parts. This embodiment differs from that of FIG. 3 in that it incorporates a weighting slug 36 approximately midway along its length.

In order to be sure that, in practical use, the pellet of the invention will remain in the rumeno-reticular sac, it is appropriate that it should have a minimum density of about 2.25 gm/ml and of course its density will usually increase as it dissolves since the active material will, normally, be less dense than the alloy of the plates 12, 32 and the metal of the slug 20, 36, when provided, and the proportion of metal to active material increases with consumption of the pellet.

The magnesium alloy of which the plates 12, 32 are made may contain from 0 to 15% of Aluminium, from 0 to 6% Copper, from 0 to 5% Zinc, from 0 to 2% Nickel and from 0 to 0.5% Cobalt, these percentages being by weight. A preferred alloy comprises 12% Aluminium, 2% Copper and 86% Magnesium.

The slug 20, 36 is preferably a Zinc-based alloy containing from 5% to 25% by weight Magnesium, which aids its eventual degradation by the rumen juices, but it may be of iron or other suitable material which will be gradually dissolved or consumed.

It will be appreciated that it is not intended to limit the invention to the above examples only, many variations, such as might readily occur to those skilled in the art, being possible, without departing from the scope of the claims appearing at the conclusion hereof.

For example, the doses 24, 34 may be provided by substances other than anthelmintics, or they may comprise other active agents in conjunction with anthelmintics.

In each of the embodiments of FIGS. 1 and 2, an additional dose (not shown) of active substance may be incorporated at the exposed end, not enclosed by the sheath or sleeve 26, 38, of the assembly 10, 30 whereby a first dose is delivered immediately upon administration of the pellet. In the embodiment of FIG. 3, the arrangement may be such that an active substance dose 34 is initially exposed at each end, or such that there is an active substance dose 34 exposed at one end and a plate 32 exposed at the other end.

Active agents incorporated in the pellets of the invention may include anti-bacterials, anti-coccidials, anti-protozoals, anti-theilerials, anti-fungals, anti-virals, insecticides, acaricides, growth promoters, nutrients, antibiotics and trace elements such as copper, cobalt, selenium and their compounds. These agents may, of course, be included separately or in combination. The preferred anthelmintic is oxfendazole, lasalocid (Trade Mark) or the compound known as M-139603 described in detail in United Kingdom Patent Specification No. 2027013B being preferred anti-coccidials. Another preferred anthelmintic is levamisole.

I claim:

1. A pharmaceutical pellet of the kind intended to be administered to a ruminant to reside in its rumeno-reticular sac and release predetermined quantities of biologically-active substance over an extended period of time characterised in that it comprises an assembly consisting of a plurality of plates, of a magnesium alloy, axially spaced to define cavities therebetween, a biologically-active substance in each said cavity, and a retaining water-impermeable sleeve or sheath protecting the assembly from attack by rumen juices except at one axial end or both axial ends thereof.

2. A pharmaceutical pellet according to claim 1 further characterised in that a weighting slug is incorporated approximately at the middle or at one axial end of the assembly.

3. A pharmaceutical pellet according to claim 2 wherein the weighting plug is at one end and is enclosed by the sleeve.

4. A pharmaceutical pellet according to claim 1 wherein each plate is in the form of a disc, the biologically-active substance being present as tablets one of which is present between each adjacent pair of said discs.

5. A pharmaceutical pellet according to claim 2 wherein a further said tablet is provided between the weighting slug and the endmost disc thereadjacent.

6. A pharmaceutical pellet according to claim 1 wherein each plate has on one face a first peripheral skirt or flange and on its other face a second skirt inwardly-spaced from its periphery, the second and first skirts respectively of adjacent said discs locating the one within the other to define respective cavities each of which accommodates a respective dose or filling of said active substance.

7. A pharmaceutical pellet according to claim 6 wherein said second and first skirts are a tight interference fit the one within the other.

8. A pharmaceutical pellet according to claim 1 wherein the sleeve or sheath is of a plastics material.

9. A pharmaceutical pellet according to claim 1 which has one axial end only thereof exposed, said exposed end containing a dose of the active agent exposed for immediate delivery upon administration of the pellet.

10. A pharmaceutical pellet according to claim 1 wherein the magnesium alloy of the plates contains 0 to 15% Aluminium, from 0 to 6% Copper, from 0 to 5% Zinc, from 0 to 25% Nickel and from 0 to 0.5% Cobalt, the percentages being by weight.

11. A pharmaceutical pellet according to claim 2 wherein the weighted slug is of iron or of a Zinc-based alloy.

12. The method of administering to a ruminant predetermined doses of biologically active substances at predetermined intervals which comprises introducing into the reticulum of a ruminant a device formed by encapsulating doses of two different biologically active substances in successive alternate layers within an insoluble sleeve closed at one end and open at the other such that alternate doses and intermediate doses are successively exposed to rumen juices exclusively of each other.

13. The method of administering into a fluid environment predetermined doses of biologically active substances at predetermined intervals which comprises introducing into said fluid environment a device formed by encapsulating doses of two different biologically active substances in successive alternate layers within an open-ended insoluble sleeve in an order such that one of the two biologically active substances is exposed at one end of the sleeve and the other of the two biologically active substances is exposed at the other open end of the sleeve.

14. The method of administering into a fluid environment predetermined doses of biologically active substances at predetermined intervals which comprises introducing into said fluid environment a device formed by encapsulating doses of two different biologically active substances in successive alternate layers within an open-ended insoluble sleeve in an arrangement such that one of the two biologically active substances is exposed at each open end exclusively of the other of said biologically active substances.

* * * * *